(12) United States Patent
Lee et al.

(10) Patent No.: US 7,776,617 B2
(45) Date of Patent: Aug. 17, 2010

(54) SIGNAL ENHANCEMENT SYSTEM WITH MULTIPLE LABELED-MOIETIES

(75) Inventors: Helen Lee, Cambridge (GB); Ling Huang, Cambridge (GB); Magda Anastassova Dineva, Cambridge (GB); Hsiang Yun Hu, Union City, CA (US)

(73) Assignee: Diagnostics for the Real World, Ltd., Sunnyvale, CA (US)

( * ) Notice: Subject to any disclaimer, the term of this patent is extended or adjusted under 35 U.S.C. 154(b) by 1007 days.

(21) Appl. No.: 10/432,036

(22) PCT Filed: Nov. 30, 2001

(86) PCT No.: PCT/GB01/05325

§ 371 (c)(1),
(2), (4) Date: Jul. 11, 2003

(87) PCT Pub. No.: WO02/44729

PCT Pub. Date: Jun. 6, 2002

(65) Prior Publication Data

US 2004/0048395 A1    Mar. 11, 2004

(30) Foreign Application Priority Data

Nov. 30, 2000  (GB) ................................. 0029154.2
Apr. 17, 2001  (GB) ................................. 0109313.7

(51) Int. Cl.
| | | |
|---|---|---|
| *C12Q 1/00* | (2006.01) | |
| *C12M 1/34* | (2006.01) | |
| *C12M 3/00* | (2006.01) | |
| *G01N 33/53* | (2006.01) | |
| *G01N 21/00* | (2006.01) | |
| *G01N 21/75* | (2006.01) | |
| *G01N 21/76* | (2006.01) | |
| *G01N 21/77* | (2006.01) | |
| *G01N 33/566* | (2006.01) | |
| *G01N 33/543* | (2006.01) | |
| *G01N 33/551* | (2006.01) | |
| *G01N 33/544* | (2006.01) | |

(52) U.S. Cl. ........................ 436/518; 435/4; 435/7.1; 435/287.1; 435/287.2; 435/288.7; 436/501; 436/524; 436/528; 436/164; 436/166; 436/169; 436/172; 436/807

(58) Field of Classification Search .................. 435/4, 435/7.1, 287.1, 287.2, 288.7; 436/501, 518, 436/524, 528, 164, 166, 169, 172, 807
See application file for complete search history.

(56) References Cited

U.S. PATENT DOCUMENTS 4,434,150 A    2/1984    Azad et al. .................... 424/1.1

(Continued)

FOREIGN PATENT DOCUMENTS

EP    0258963    3/1988

(Continued)

*Primary Examiner*—Gailene R Gabel
*Assistant Examiner*—Jacqueline Diramio
(74) *Attorney, Agent, or Firm*—Seed IP Law Group PLLC

(57) ABSTRACT

Dipstick tests for detecting analyte are described. In a preferred embodiment, a multiple biotinylated antibody capable of binding analyte is bound to an anti-biotin antibody labelled with colloidal gold and wicked up the dipstick with test solution thought to contain analyte. Complex formed between analyte, biotinylated anti-analyte antibody, and colloidal gold labelled anti-biotin antibody is captured at a capture zone of the dipstick. Presence of colloidal gold label at the capture zone indicates the presence of analyte in the test solution. The sensitivity of analyte detection using such methods is an order of magnitude higher than for comparable methods in which biotinylated anti-analyte antibody bound to analyte is wicked up the dipstick in a first step, and a colloidal gold labelled anti-biotin antibody is wicked up the dipstick in a separate step. Kits for performing the tests of the invention are also described.

8 Claims, 11 Drawing Sheets

U.S. PATENT DOCUMENTS

| | | | |
|---|---|---|---|
| 4,943,522 A | 7/1990 | Eisinger et al. | 435/7 |
| 5,073,484 A | 12/1991 | Swanson et al. | 435/7.92 |
| 5,089,423 A * | 2/1992 | Diamandis et al. | 436/518 |
| 5,188,937 A | 2/1993 | Schulte et al. | 435/7.36 |
| 5,252,459 A * | 10/1993 | Tarcha et al. | 435/6 |
| 5,770,460 A | 6/1998 | Pawlak et al. | 436/510 |
| 5,773,234 A | 6/1998 | Pronovost et al. | 435/7.36 |
| 5,895,750 A * | 4/1999 | Mushahwar et al. | 435/7.5 |
| 6,146,589 A | 11/2000 | Chandler | 422/58 |
| 6,803,196 B1 * | 10/2004 | Lyon et al. | 435/6 |
| 2003/0143639 A1 * | 7/2003 | Matsushita et al. | 435/7.9 |
| 2004/0137493 A1 * | 7/2004 | Goldberg et al. | 435/6 |
| 2008/0206853 A1 * | 8/2008 | Lee et al. | 435/287.2 |

FOREIGN PATENT DOCUMENTS

| | | |
|---|---|---|
| EP | 0354847 | 2/1990 |
| EP | 0387027 | 9/1990 |
| EP | 0813064 | 12/1997 |
| WO | WO 94/11734 | 5/1994 |
| WO | WO96/19731 | 6/1996 |
| WO | WO96/24060 | 8/1996 |
| WO | WO98/18488 | 5/1998 |
| WO | WO98/36278 | 8/1998 |
| WO | WO 99/58948 | 11/1999 |
| WO | WO00/25135 | 5/2000 |

* cited by examiner

Figure 3

| Dipstick assay | Concentration of CT-LPS (pg/test) | | | | | |
|---|---|---|---|---|---|---|
| | 420 | 125 | 40 | 15 | 5 | NC* |
| Direct (Prior art) | | | | | | |
| Indirect (Signal enhanced) | | | | | | |

*NC: negative control

| Dipstick assay | HBsAg (ng/ml) | | | | | | | |
|---|---|---|---|---|---|---|---|---|
| | 12.5 | 6.25 | 3.12 | 1.56 | 0.78 | 0.39 | 0.195 | NC* |
| Direct (Prior art) |  |  |  |  |  |  |  |  |
| Indirect (Signal enhanced) |  |  |  |  |  |  | | |

* NC: negative control

| Assay Format | Concentration of CT-LPS (µl/test) | | | | | |
|---|---|---|---|---|---|---|
| | 0.1 | 0.03 | 0.01 | 0.003 | 0.001 | 0 |
| Direct detection (Prior art) | | | | | | |
| Indirect detection (Signal enhanced) 2 biotin/Ab | | | | | | |
| 4 biotin/Ab | | | | | | |
| 6 biotin/Ab | | | | | | |
| 8 biotin/Ab | | | | | | |
| 9 biotin/Ab | | | | | | |
| 10 biotin/Ab | | | | | | |
| 11 biotin/Ab | | | | | | |
| 12 biotin/Ab | | | | | | |

1µl contains 4.218ng of LPS

FIGURE 7

| Assay Format | Concentration of CT-LPS (µl/test) | | | | | |
|---|---|---|---|---|---|---|
| | 0.1 | 0.03 | 0.01 | 0.003 | 0.001 | 0 |
| 6 biotin/Ab | | | | | | |
| 9 biotin/Ab | C T | | | | | |
| 12 biotin/Ab | | | | | | |
| 14 biotin/Ab | | | | | | |
| 18 biotin/Ab | | | | | | |
| 20 biotin/Ab | | | | | | |

1µl contains 4.218ng of LPS
C = Procedural control
T = Test line

FIGURE 8

| Assay Format | Concentration of CT-LPS (µl/test) | | | | | |
|---|---|---|---|---|---|---|
| | 0.1 | 0.03 | 0.01 | 0.003 | 0.001 | 0 |
| One-step (Signal enhanced) C T | | | | | | |
| Two-step (Prior art) C T | | | | | | |

1µl contains 4.218ng of LPS

C = Procedural control

T = Test line

FIGURE 9

| Assay Format | Concentration of CT-LPS (μl/test) | | | | | |
|---|---|---|---|---|---|---|
| | 0.1 | 0.03 | 0.01 | 0.003 | 0.001 | 0 |
| Direct detection (Prior art) | | | | | | |
| Indirect detection (Signal enhanced) 6 FITC/Ab | | | | | | |
| 7 FITC/Ab | | | | | | |
| 9 FITC/Ab | | | | | | |
| 11 FITC/Ab | | | | | | |

1μl contains 4.218ng of LPS

FIGURE 10

SIGNAL ENHANCEMENT SYSTEM WITH MULTIPLE LABELED-MOIETIES

This application is a 371 of PCT/GB01/05325 filed on Nov. 30, 2001, the entirety of which is hereby incorporated by reference.

FIELD OF THE INVENTION

This invention relates to methods for testing for the presence of an analyte in a test solution and to kits for carrying out such methods.

BACKGROUND OF THE INVENTION

One conventional method for testing for the presence of an analyte in a test solution comprises capturing the analyte on a dipstick and detecting for the presence of the analyte on the dipstick. The dipstick has a contact end for contacting the test solution and a capture zone remote from the contact end to which an anti-analyte antibody (the capture antibody) is immobilized.

To test for the presence of analyte, the contact end of the dipstick is contacted with the test solution. If analyte is present in the test solution it travels to the capture zone of the dipstick by capillary action where it is captured by the capture antibody. The presence of analyte at the capture zone of the dipstick is detected by a further anti-analyte antibody (the detection antibody) labelled with, for example, colloidal gold.

These dipstick tests have several advantages. They are easy and cheap to perform, no specialist instruments are required, and the results are obtained rapidly and can be read visually. These tests are, therefore, particularly suited for use in a physician's office, at home, in remote areas, and in developing countries where specialist equipment may not be available. They can be used, for example, to test whether a patient is infected with a disease causing micro-organism such as *Chlamydia trachomatis*.

However, the sensitivity of analyte detection using such tests is relatively low. Consequently, if the analyte is only present in small amounts in the test solution it can remain undetected. This is a particular disadvantage if the test is being used to diagnose whether or not a patient has a particular disease as the patient may not be diagnosed as having that disease. This is particularly the case where the patient is asymptomatic, but also where symptoms are present but it is necessary to confirm that these are caused by a particular disease, or particular disease strain.

WO 00/25135 discloses a two-step dipstick detection system for detecting antigen. The detection system uses an anti-antigen biotinylated antibody and an anti-biotin antibody labelled with colloidal gold (anti-biotin gold conjugate). In the first step, the biotinylated antibody is mixed with the test solution and the tip of the dipstick membrane is then immersed in the mixture so that the aqueous mixture wicks up the membrane by capillary action. Antigen in the mixture bound to the biotinylated antibody is captured by an immobilised anti-antigen antibody at a capture zone of the dipstick to form a complex comprising the immobilised anti-antigen antibody, the antigen and the biotinylated antibody. In the second step, the dipstick is immersed in a separate suspension of anti-biotin gold conjugate. The anti-biotin gold conjugate wicks up the membrane by capillary action and binds to biotinylated antibody captured with the antigen at the capture zone. Antigen is then detected by the presence of gold label at the capture zone.

Whilst the two-step system may provide increased sensitivity, it is desired to further improve the sensitivity of analyte detection.

SUMMARY OF THE INVENTION

According to a first aspect of the invention there is provided a method for testing for the presence of an analyte in a test solution which comprises the following steps:
a) providing a chromatographic strip having a contact end for contacting the test solution and a capture moiety immobilised at a capture zone of the chromatographic strip remote from the contact end, the capture moiety comprising a member of a ligand/anti-ligand binding pair capable of binding (other than by nucleic acid base pairing interaction) the analyte, or a derivative thereof, as the other member of the ligand/anti-ligand binding pair;
b) contacting a targeting agent, capable of binding the analyte or derivative thereof, with the test solution to allow binding of the targeting agent to analyte or derivative in the test solution, the targeting agent being provided with a plurality of ligands;
c) binding a label to each of two or more ligands of the targeting agent;
d) contacting the contact end of the chromatographic strip with the test solution to allow analyte, or derivative thereof, bound to the labelled targeting agent to travel to the capture zone by capillary action and be captured by the capture moiety; and
e) detecting for the presence of label at the capture zone.

According to the invention the targeting agent is bound to the labels to form the labelled targeting agent before it contacts the capture zone. This is in contrast to the method of WO 00/25135 in which the biotinylated antibody and the anti-biotin gold conjugate are wicked up the dipstick membrane in two separate steps. The sensitivity of analyte detection using methods of the invention has surprisingly been found to be greater than the two-step method of WO 00/25135. Under optimal conditions, the sensitivity of analyte detection is at least an order of magnitude higher than the sensitivity of detection using the two-step method.

DETAILED DESCRIPTION OF THE INVENTION

To perform a method of the first aspect of the invention, the targeting agent and labels may simply be added to the test solution and the test solution then contacted with the contact end of the chromatographic strip. Such methods are easier to perform than the method disclosed in WO 00/25135 in which two separate wicking steps are required. The results may, therefore, be obtained more rapidly, and yet the sensitivity of analyte detection is higher.

The term "chromatographic strip" is used herein to mean any porous strip of material capable of transporting a solution by capillarity. The chromatographic strip may be capable of bibulous or non bibulous lateral flow, but preferably bibulous lateral flow. By the term "non-bibulous lateral flow" is meant liquid flow in which all of the dissolved or dispersed components of the liquid are carried at substantially equal rates and with relatively unimpaired flow laterally through the membrane as opposed to preferential retention of one or more components as would occur with "bibulous lateral flow". Materials capable of bibulous lateral flow include paper, nitrocellulose, and nylon. A preferred example is nitrocellulose.

The labels may be bound to the ligands of the targeting agent by pre-mixing the targeting agent with the labels before the targeting agent is added to (or otherwise contacted with) the test solution. However, in some circumstances, it is preferred that the targeting agent and labels are not pre-mixed because such pre-mixing can cause the targeting agent and labels to precipitate. Thus, the targeting agent and the labels may be added separately to (or contacted separately with) the test solution. The targeting agent and the labels can be added to (or contacted with) the test solution at substantially the same time, or in any order.

The test solution may be pre-incubated with the targeting agent and labels before the test solution is contacted with the contact end of the chromatographic strip to ensure complex formation. The optimal time of pre-incubation will depend on the ratio of the reagents and the flow rate of the chromatographic strip. In some cases, pre-incubation for too long can decrease the detection signal obtained, and even lead to false positive detection signals. Thus, it may be necessary to optimise the pre-incubation time for the particular conditions used.

It may be desired to pre-incubate the targeting agent with the test solution before binding the labels to the targeting agent so that the targeting agent can be allowed to bind to analyte in the test solution under optimum binding conditions.

In alternative aspects of the invention, binding of the labels to the targeting agent may take place on the chromatographic strip. This can be achieved by releasably immobilising the labels and/or targeting agent to the chromatographic strip at a conjugate zone between the contact end and the capture zone. The labels and/or targeting agent are then released into test solution as it travels by capillary action to the capture zone. If the labels, but not the targeting agent, are releasably immobilised, the targeting agent should be contacted with the test solution so that targeting agent in the test solution can bind to the labels as they are releasably immobilised. Similarly, if the targeting agent is releasably immobilised, but not the labels, the labels should be contacted with the test solution.

Thus, according to a second aspect of the invention there is provided a method for testing for the presence of an analyte in a test solution which comprises the following steps:

a) providing a chromatographic strip having:

i) a contact end for contacting the test solution;

ii) a capture moiety immobilised at a capture zone of the chromatographic strip remote from the contact end, the capture moiety comprising a member of a ligand/anti-ligand binding pair capable of binding (other than by nucleic acid base pairing interaction) the analyte, or a derivative thereof, as the other member of the ligand/anti-ligand binding pair; and iii) a targeting agent releasably immobilised at a conjugate zone of the chromatographic strip between the contact end and the capture zone, the targeting agent being provided with a plurality of ligands and being capable of binding the analyte or derivative thereof;

b) contacting a plurality of labels with the test solution;

c) contacting the contact end of the chromatographic strip with the test solution to allow test solution to travel through the conjugate zone to the capture zone, thereby releasing targeting agent from the conjugate zone so that each of two or more ligands of the released targeting agent are bound by a label and so that released targeting agent bound to the labels can travel with analyte or derivative in the test solution to the capture zone and be captured at the capture zone as part of a complex formed between the capture moiety, analyte or derivative, the targeting agent, and the labels; and d) detecting for the presence of label at the capture zone.

Alternatively, the labels may be releasably immobilised to the conjugate zone of the chromatographic strip, and the targeting agent contacted with the test solution, or both the labels and the targeting agent may be releasably immobilised to the conjugate zone.

Immobilisation may be carried out simply by drying the labels and/or targeting agent onto the chromatographic strip. An advantage of releasably immobilising some or all of the reagents necessary to perform a method of the invention onto the chromatographic strip is that these reagents do not then need to be added separately to the test solution, nor carried or packaged separately with the other components necessary to perform the method.

In other aspects of the invention, it may be desirable to contact the contact end of the chromatographic strip with a solution containing the labelled targeting agent after the contact end has been contacted with the test solution, or to contact the targeting agent and labels with the test solution after analyte or derivative has been allowed to travel by capillary action to the capture zone, so that labelled targeting agent travels by capillary action to the capture zone separately from the analyte or derivative.

A possible advantage of such aspects is that any non specific binding of labels to the chromatographic strip can be reduced because more of the test solution (or solution containing the targeting agent) travels through the chromatographic strip, thereby washing the chromatographic strip.

In other aspects of the invention, the labelled targeting agent may be contacted directly with the capture zone of the chromatographic strip after analyte or derivative has been captured by the capture moiety. Binding of the labels to the ligands of the targeting agent should be carried out before (or, exceptionally, as) the targeting agent is contacted with the capture zone.

Thus, in its broadest sense a method of the invention for testing for the presence of an analyte in a test solution comprises the following steps:

a) providing a chromatographic strip having a contact end for contacting the test solution and a capture moiety immobilised at a capture zone of the chromatographic strip, the capture moiety comprising a member of a ligand/anti-ligand binding pair capable (other than by nucleic acid base pairing interaction) of binding the analyte, or a derivative thereof, as the other member of the ligand/anti-ligand binding pair;

b) contacting the contact end of the chromatographic strip with the test solution to allow analyte, or derivative thereof, to travel to the capture zone by capillary action and be captured by the capture moiety;

c) contacting a labelled targeting agent with the capture zone, the labelled targeting agent being capable of binding the analyte, or a derivative thereof, thereby allowing labelled targeting agent to be captured at the capture zone as part of a complex comprising the capture moiety, the analyte or derivative and the labelled targeting agent, wherein the labelled targeting agent comprises a plurality of ligands and each of two or more ligands are bound to a label; and d) detecting for the presence of label at the capture zone.

In some aspects and embodiments of the invention, it may be desirable for the labels and/or the targeting agent to be in dry form, for example as a powder or tablet which is contacted with the test solution. This has the advantage that kits for performing methods of the invention can be reduced in weight and size because they do not need to include separate solutions of the labels and/or targeting agent. This adds to the ease of use of kits of the invention, and can be important if the kits are to be transported, particularly to remote areas. A further advantage is that the targeting agent and/or label may be more stable in dry form. This may be particularly important when methods of the invention are performed in areas where it may be difficult to freeze or cool solutions of reagents which would otherwise be unstable at room temperature.

Preferably the targeting agent has at least 4 ligands, more preferably at least 6 ligands. Preferably the targeting agent has no more than So ligands. The optimum number of ligands may depend on the identity of the targeting agent. For example, for a targeting agent comprising IgG, the number of ligands preferably does not exceed 20 per IgG molecule. However, for a targeting agent comprising IgM, more ligands may be used.

We have found that the optimum number of ligands of the targeting agent depends on the flow rate of the chromatographic strip. In general, the faster the flow rate, the higher the number of ligands per targeting agent.

The flow rate of the membrane depends on the pore size, pore structure, and the surfactant treatment of the membrane. In untreated nitrocellulose membranes, flow rates are influenced by pore size: the larger the pore, the faster the flow rate. However, post treatments and blocking solutions can also have significant impact on the flow rate. Different solutions may also flow along a membrane at different rates, whether by virtue of their viscosity or particulate content.

A fast flow rate membrane is defined here as a membrane in which water travels by capillary action at a rate of about 70-80 seconds per 40 mm. Examples of fast flow rate membranes are: Whatman Purabind A-RP membrane (pore size 8 μm)–water flow rate=80 seconds per 40 mm; and WhatMan Purabind A-XP membrane (pore size 12 μm)–water flow rate=70 seconds per 40 mm. An example of a slower flow rate membrane is Schleicher & Schuell AE99 membrane (pore size 8 μm)–water flow rate=130 seconds per 40 mm.

For fast flow rate membranes, optimum results are obtained with about 9-20 ligands per targeting agent, preferably about 14-18. For slower flow rate membranes optimum results are obtained with about 6-12 ligands per targeting agent, more preferably 8-12 ligands, even more preferably 8-10 ligands, and most preferably 8 or 9 ligands.

We have found that the optimum number of ligands of the targeting agent depends on the viscosity of the biological sample. In general, the more viscous the sample type, the lower the number of ligands per targeting agent. For example, where a method of the invention is used to detect CT, typical test samples are urine, endocervical swab, or urethral swab. These samples have different viscosities, so the optimum number of ligands per targeting agent used will depend on the viscosity of the sample solution.

The targeting agent may comprise a single moiety, or more than one moiety. For example the targeting agent may comprise: a primary moiety capable of binding to the analyte or derivative; and a secondary moiety capable of binding to the primary moiety, the secondary moiety being provided with a plurality of ligands.

Preferred ligands include biotin (which can be bound by anti-biotin antibody, avidin, streptavidin, or a derivative thereof), fluorescein (which can be bound by anti-fluorescein antibody) and DNP (which can be bound by anti-DNP antibody).

The or each moiety of the targeting agent is preferably an antibody. The term "antibody" as used herein means any antibody or antibody fragment (whether produced naturally or recombinantly) which retains antigen binding activity. This includes a monoclonal or polyclonal antibody, a single chain antibody, a Fab fragment of a monoclonal or polyclonal antibody, and a chimeric antibody.

In a preferred embodiment, the targeting agent comprises a primary antibody capable of binding to the analyte or derivative, and a secondary antibody capable of binding to the primary antibody, the secondary antibody being covalently coupled to a plurality of ligands. This embodiment is preferred because the secondary antibody can be prepared separately and used with different primary antibodies for detecting different analytes.

A plurality of labels are preferably bound to at least one of the ligands of the targeting agent, thereby further increasing the sensitivity of analyte detection.

Any labels which, when part of a complex formed between the capture moiety, analyte or derivative, the targeting agent and the labels, allow detection of the complex on the chromatographic strip may be used. Preferred labels are visually detectable labels. Examples of suitable visually detectable labels include textile dyes and coloured particles such as coloured latex particles and metal sol such as colloidal gold or selenium. Colloidal gold with a size range of about 20-60 nm is preferred, more preferably 20-40 nm. Similar assay sensitivities can be obtained using colloidal gold with a narrow size distribution, from 23-31 nm (30 nm British Biocell International Limited), or a wide size distribution, from 20-47 nm (average 29-38 nm).

Examples of other suitable labels include radioactive labels, luminescent labels particularly fluorescent labels, and labels comprising an enzyme capable of reacting with a chromogenic substrate or with a substrate which is converted into a luminescent product by the enzyme. Such chemiluminescent labels are particularly preferred because the strength of the luminescent signal generated is high in relation to other labels, thereby enhancing the sensitivity of analyte detection.

Each label may be provided by a labelling agent. Each labelling agent may comprise a single moiety or more than one moiety. For example, a labelling agent may comprise: a primary moiety capable of binding to a ligand of the targeting agent; and a labelled secondary moiety capable of binding to the primary moiety.

The or each moiety of the labelling agent is preferably an antibody.

In a preferred embodiment, the labelling agent comprises a primary antibody capable of binding to a ligand of the targeting agent and a secondary antibody capable of binding to the primary antibody, the secondary antibody being coupled to a label. This embodiment is preferred because the secondary antibody can be prepared separately and used with different primary antibodies for binding to different ligands.

For embodiments in which the ligands of the targeting agent comprise biotin, suitable labelling agents include the following:
i) a labelled anti-biotin antibody;
ii) a labelled moiety comprising avidin, streptavidin, or a derivative thereof which retains biotin binding activity;
iii) an anti-biotin antibody, avidin, streptavidin, or a derivative thereof which retains biotin binding activity (the primary moiety) and a labelled antibody (the secondary moiety) capable of binding to the primary moiety.

Each labelling agent may preferably comprise a plurality of labels to further enhance the sensitivity of detection. This may be achieved by covalently coupling a plurality of labels to each labelling agent. Alternatively, if the labelling agent comprises more than one moiety, each moiety may be labelled, as shown in FIG. 5C.

The capture moiety may comprise a single moiety or a plurality of moieties non covalently bound together. The capture moiety may comprise an antibody capable of binding the analyte or derivative thereof.

In other embodiments, the analyte may be an antibody and the capture moiety an antigen. Such embodiments can be particularly advantageous for testing whether or not an individual has been infected with a disease causing micro-organism if the amount of antigen of that disease causing micro-organism in the test solution is likely to be very low. Antibodies produced by the individual to the antigen in response to infection by the micro-organism may instead be present at much higher amounts, thereby making detection of the antibodies a more sensitive way of diagnosing infection. Examples are antibodies produced in response to HIV infection.

A derivative of the analyte may be formed by chemically modifying the analyte for example by covalently coupling the analyte to a ligand which can be bound by the capture moiety. In one embodiment, the analyte could be covalently coupled to biotin to form a derivative of the analyte which can then be captured by a capture moiety comprising an anti-biotin antibody, avidin, streptavidin, or a biotin binding derivative thereof. Alternatively, the analyte may be formed by non covalently binding a derivatising moiety, such as an antibody, to the analyte which can be bound by the capture moiety.

An advantage of forming a derivative of the analyte is that the analyte and labelled targeting agent may be further spaced from the chromatographic strip, thus reducing or preventing any steric hindrance which might otherwise occur between the chromatographic strip and an analyte-containing complex captured at the capture zone. Capture of an analyte derivative also allows identical chromatographic strips to be used to capture different analytes if the analyte derivative comprises a capture ligand which can be bound by the capture moiety of such strips.

In preferred embodiments, the analyte derivative comprises a plurality of capture ligands, each of which can be bound by the capture moiety. The presence of a plurality of capture ligands increases the probability that the analyte derivative will be captured by the capture moiety.

Examples of preferred embodiments in which the analyte is bound by a derivatising moiety are shown in FIG. 6. Note that in this figure, binding of analyte by labelled targeting moiety is not shown.

Methods of the invention may be used to test for any suitable analyte. Examples include antigens of infectious agents or antibodies raised against such antigens, hormones (for example as a pregnancy test), metabolites (for example to test for metabolic disorders), drugs (therapeutic or illicit), vitamins, steroids, or antibodies produced as part of an allergic reaction.

Preferred examples of antigens of infectious agents or antibodies to such antigens are: hepatitis B virus surface antigen (HBsAg), HBsAg 'a' epitope, hepatitis B 'e' antigen (HBeAg), antibodies to HBeAg, antibodies to hepatitis B core antigen (e.g. anti hepatitis B core antigen-IgG and -IgM), hepatitis C virus (HCV) antigens, antibodies to HCV antigens, HIV antigens (of HIV 1 or HIV 2), antibodies to HIV antigens, *Chlamydia trachomatis* antigens, or *Neisseria gonorrhea* antigens.

There are also provided according to the invention kits for performing methods of the invention.

A kit for performing a method of the first aspect of the invention comprises:
i) a chromatographic strip having a contact end for contacting the test solution and a capture moiety immobilised at a capture zone of the chromatographic strip remote from the contact end, the capture moiety comprising a member of a ligand/anti-ligand binding pair capable of binding (other than by nucleic acid base pairing interaction) the analyte, or a derivative thereof, as the other member of the ligand/anti-ligand binding pair;
ii) separately from the chromatographic strip, a targeting agent capable of binding the analyte or derivative thereof, the targeting agent being provided with a plurality of ligands, and a plurality of labelling agents each bound to a ligand of the targeting moiety, each labelling agent being provided with a label.

A kit for performing a method of the second aspect of the invention comprises:
i) a chromatographic strip having: a contact end for contacting the test solution; a capture moiety immobilised at a capture zone of the chromatographic strip remote from the contact end, the capture moiety comprising a member of a ligand/anti-ligand binding pair capable of binding (other than by nucleic acid base pairing interaction) the analyte, or a derivative thereof, as the other member of the ligand/anti-ligand binding pair; and a targeting agent releasably immobilised at a conjugate zone of the chromatographic strip between the contact end and the capture zone, the targeting agent being provided with a plurality of ligands and being capable of binding the analyte or derivative thereof; and separately
ii) a plurality of labelling agents capable of binding to a ligand of the targeting moiety, each labelling agent being provided with a label.

The labelling agents may be releasably immobilised to the conjugate zone of the chromatographic strip as well as the targeting agent. Alternatively, the labelling agents may be immobilised to the chromatographic strip instead of the targeting agent.

Where the kit is for performing a method of the second aspect of the invention, it will be appreciated that releasably immobilising the targeting agent and the labelling agents to the conjugate zone of the chromatographic strip has the particular advantage that all the reagents necessary for testing for the presence of the analyte in the test solution are present on the chromatographic strip (provided that labelling agents are chosen which do not require reaction with further reagents to visualise the complex captured at the capture zone, unless these further reagents are also releasably immobilised to the chromatographic strip).

In such embodiments, it will be necessary to ensure that there is sufficient distance between the conjugate zone and the capture zone for the labelling agents to be able to bind to the targeting agent as they travel to the capture zone once they have been released. Alternatively, the conjugate zone should be immersed in the test solution to allow release of the targeting agent and the labelling agents into the test solution so that they can bind to each other in the test solution before travelling by capillary action to the capture zone.

Where the targeting agent and the labelling agents are releasably immobilised to the conjugate zone of the chromatographic strip, they may be immobilised to the same part of the conjugate zone or at different zones within the conjugate zone. Where the targeting agent and the labelling agents are immobilised to the same part of the conjugate zone, they may be interspersed with one another at the conjugate zone, or they may be in different layers.

In one arrangement it may be preferred for the labelling agents to be immobilised directly to the chromatographic strip at the conjugate zone, thereby forming a first layer, and the targeting agent to be immobilised to the first layer, thereby forming a second layer on top of the first layer. A possible advantage of this arrangement is that the targeting agent would be expected to be released into the test solution before the labelling agents. This may be of importance to ensure efficient complex formation at the capture zone if it is suspected that the labelling agents could interfere with binding of the targeting agent to analyte or derivative.

Where the targeting agent and/or the labelling agent are not immobilised to the chromatographic strip, they may preferably be in dry form, for example as a powder or a tablet.

The sensitivity of analyte detection may depend on the ratio of the targeting agent to the labelling agent. Consequently, the ratio should be chosen to obtain optimum results.

Where kits of the invention comprise a targeting agent consisting of more than one moiety, it may in some circumstances be desirable for one or more of the moieties to be releasably immobilised to the chromatographic strip and one or more of the remaining moieties to be separate from the chromatographic strip. Similarly, where each labelling agent comprises one or more moieties, it may in some circumstances be desirable for one or more of the moieties to be releasably immobilised to the chromatographic strip and one or more of the remaining moieties to be separate from the chromatographic strip.

Kits of the invention in which a further reagent(s) is required for detection of a captured complex containing the labelling agent (for example, those kits in which the labelling agents comprise an enzyme capable of converting a chromogenic substrate or a substrate which is converted to a luminescent product by the enzyme) preferably further comprise the reagent(s) required for detection.

For those aspects and embodiments of the invention in which the targeting agent and/or the labels are releasably immobilised to a conjugate zone of the chromatographic strip, the concentration of the labels and/or the targeting agent in the test solution arriving at the capture zone by capillary action is likely to vary. This is because the concentration of the targeting agent and/or labels in the test solution will rise and fall as the releasably immobilised targeting agent and/or labelling agent is released into the test solution until there is none of the reagent(s) left at the conjugate zone.

As the concentration of the targeting agent and/or the labels increases at the capture zone, there may be an excess amount of the targeting agent and/or the labels for optimal formation of complex at the capture zone. In contrast, when the concentration of the targeting agent and/or the labels is lower, there may be insufficient amounts of the targeting agent and/or the labels at the capture zone. Consequently, the total amount of complex captured at the-capture zone may be less than the total amount captured when the contact end of the chromatographic strip is contacted with test solution containing an optimal concentration of the targeting agent and/or the labels. The sensitivity of detection may, therefore be reduced.

Thus, it may be preferred that the targeting agent and/or labels are not releasably immobilised to a conjugate zone of the chromatographic strip.

There is also provided according to the invention use of a kit of the invention to test for the presence of an analyte in a test solution.

There is also provided according to the invention a labelled targeting agent for testing for the presence of an analyte in a test solution, the labelled targeting agent being capable of binding the analyte or a derivative thereof but not being bound to the analyte or derivative, wherein the labelled targeting agent is provided with a plurality of ligands, each ligand capable of being bound by a label to allow detection of the labelled targeting agent utilising the labels. The invention further provides use of a labelled targeting agent of the invention to test for the presence of an analyte in a test solution.

Embodiments of the invention are illustrated with reference to FIG. 1. In the following discussion, the primary antibody corresponds to the targeting agent, the haptens correspond to the ligands of the targeting agent, the labelled secondary antibody corresponds to the labelling agent, and the capture antibody corresponds to the capture moiety.

The major disadvantage of any membrane-based rapid assay is its reduced sensitivity compared with that of enzyme-linked immunoassay (EIA). This reduced sensitivity is due to the fact that, in a rapid assay, antigen-antibody reaction must reach completion within 15 to 20 minutes without the benefit of alternate washing and incubation steps. In addition, the antigen-antibody complex is detected by visual readout, without the help of signal amplification by enzymatic reactions. The combination of the reduction in sensitivity inherent in the rapid assay format with that due to limited sample volume must be compensated for in an improved test system.

It is intended to amplify the detection signal by chemically coupling multiple copies (N) of a hapten, such as biotin or fluorescein, to the primary antibodies, which will be targeted to an analyte to be tested. This, together with labelling of the secondary antibodies (anti-hapten) with a label such as coloured particles (for example colloidal gold), will increase the detection signal.

FIG. 1 shows a comparison of assay sensitivity between a direct assay without amplification (prior art) and an indirect detection system with amplification according to the invention.

In FIG. 1 the analyte to be tested for is CT-lipopolysaccharide (CT-LPS). In the prior art assay without amplification (direct detection, without signal enhancement according to the invention), a labelled antibody is targeted to a specific antigen on the analyte. In FIG. 1A this is shown as an anti-LPS antibody attached to colloidal gold. The antibody can react with the specific antigen (e.g. LPS) on an analyte (e.g. CT-LPS) in a liquid sample and bind it. In order to detect the analyte when bound to the labelled antibody, an immobilised capture antibody is used. This is shown in FIG. 1A also as an anti-LPS antibody which recognises a different specific antigen on the same analyte.

The CT-LPS analyte (shown as reference 1 in FIG. 1A) is multimeric. It is extracted from CT bacteria, for example by detergent or heat treatment. The capture antibody and the labelled antibody bind to a different part of the CT-LPS multimer.

According to the invention, the primary antibody specific for the analyte is not labelled directly (indirect detection). The primary antibody is provided with multiple copies (preferably 3-9) of a hapten, particularly biotin. The multiple haptens on the primary antibody can be targeted by anti-hapten labelled secondary antibodies. In the example of FIG. 1B these are anti-biotin antibodies with colloidal gold labels. Multiple secondary antibodies can bind to a single primary antibody, leading to amplification of the number of labels per analyte. The conjugate of the analyte and the primary antibody (labelled with secondary antibodies) can then be captured and detected in the conventional manner using a capture antibody.

It is to be expected that detection of analyte according to these embodiments of the invention would normally be carried out by first reacting the primary antibody with a sample to be tested (which may or may not contain the analyte). Once primary antibody has reacted with any analyte present, it can then subsequently be labelled with the secondary antibody.

The conjugate of any analyte with the primary antibody and secondary antibody labels can then be captured by a capture antibody.

However, it is not absolutely essential to the underlying principle of the invention that the antibody-antigen and antibody-hapten reactions be carried out in exactly this order. Those of skill in the art will appreciate that under certain circumstances it might be possible or even preferable to react a secondary labelled antibody with the primary unlabelled analyte-targeting antibody as a first step, followed by reaction of the conjugate with any analyte in a test sample and subsequent capture of the labelled analyte.

It is also not excluded that there might be the possibility of firstly capturing any analyte on the capture antibody and subsequently carrying out the primary and secondary antibody binding reactions (in whichever order is appropriate), as long as the primary and secondary antibodies are bound to each other before reaching the capture zone.

It will be appreciated that in certain circumstances it may be an advantage to have a first reaction step in which the anti-analyte antibody (or targeting agent) has optimal conditions (time, temperature, reagents etc) in which to react with any analyte present in a sample. This may particularly be the case where the analyte is in low concentration in a sample or is in some way difficult to access by the primary antibody.

In such circumstances the best possible binding conditions for the primary antibody may be found giving the best possibility of detecting analyte in a sample. Thus, it will be appreciated that there may be conditions which will favour binding of an unlabelled primary antibody to an analyte over the binding of a labelled primary antibody to an analyte (as would be the case in the prior art direct labelling method).

Furthermore, since the avidity of the secondary antibody (or labelling agent) carrying the label for the hapten on the primary antibody (according to the invention) may be very high, it is another potential advantage of the invention that it is feasible to use relatively low concentrations of labelled antibody whilst yet obtaining relatively high levels of (amplified) label attachment (via the primary antibody/secondary antibody conjugate attachment to the analyte).

We have also recognised that in the prior art, direct labelling method, the label (e.g. the coloured particle: colloidal gold) may be attached via the antibody in quite close proximity to the analyte target (i.e. the LPS). This is shown schematically in FIG. 1A. For example a separation between the analyte and the gold particle of about 12 nm is a possibility. In contrast, when using a primary antibody of the type shown in FIG. 1, with multiple haptens and using anti-hapten labelled secondary antibodies, it is possible to increase the separation between the analyte and the label. For example a separation of about 24.2 nm is possible.

Thus, in this invention, in the embodiment shown in FIG. 1B, it is most likely that the signal amplification (i.e. signal enhancement) is due to not only more coloured particles captured by the capture antibody, but also reduced steric hindrance encountered when gold-labelled antibody binds to the epitope of specific antigen. In other words, increasing the space between coloured particles and antigenic sites will reduce the steric hindrance and allow more coloured particles to accumulate at the capture zone.

A further possible reason for the enhanced sensitivity of detection achieved with methods and kits of the invention may arise from an increased probability of binding of label to the targeting agent due to the presence of the plurality of ligands of the targeting agent.

In other embodiments of the invention, the analyte may be an antibody, for example an antibody raised by an individual against an antigen of an infecting micro-organism such as HIV. In such embodiments, the primary antibody (again provided with multiple copies of a hapten, such as biotin or fluorescein) is targeted to the analyte antibody. As in other embodiments described, the multiple haptens on the primary antibody can be targeted by labelled anti-hapten secondary antibodies, thereby allowing amplification of the number of labels per analyte. However, in order to capture a conjugate of the analyte and the primary antibody (labelled with secondary antibodies), an immobilised capture antigen is used which can be targeted by the analyte antibody.

Where the analyte is a human antibody, the primary antibody may be an anti-human Fc antibody or an anti-human antibody, e.g. IgG, IgM, or a fragment thereof.

Further preferred embodiments of the invention are shown in FIG. 5.

It should be noted that the embodiments of the invention illustrated in FIGS. 1 and 5 are schematic. In reality, the labels may be much larger in relation to the other components than is shown and each label may have several moieties associated with it.

BRIEF DESCRIPTION OF THE DRAWINGS

Further embodiments of the invention are now described by way of example only, with reference to the accompanying drawings in which:

FIG. 3 shows results obtained by testing for *Chlamydia trachomatis* using a conventional method (direct detection) and a method of the invention (indirect detection);

FIG. 7 shows a comparison of the sensitivity of analyte detection using an indirect detection method with that for direct detection, and the effect on indirect detection of varying the number of ligands per anti-analyte antibody;

FIG. 8 shows the effect on the sensitivity of analyte detection by varying the number of ligands per anti-analyte antibody when a fast flow rate dipstick membrane is used;

FIG. 9 shows a comparison of the sensitivity of analyte detection for one-step and two-step detection assays;

FIG. 10 shows the results of analyte detection using a FITC coupled to anti-analyte antibody.

In the following examples, direct detection refers to analyte detection using a prior art method of analyte detection similar to that described with reference to FIG. 1A. Indirect detection refers to analyte detection using a method of the invention. Details of the method used are given in each example.

EXAMPLES

Example 1

Signal Enhancement using an Anti-Lipopolysaccharide (LPS) Antibody Coupled to Biotin in a Dipstick Immunoassay to Test for *Chlamydia trachomatis* (CT).

Aim

To investigate the sensitivity of detection of CT using an anti-LPS monoclonal antibody coupled to biotin (as a targeting agent) and a colloidal gold labelled anti-biotin monoclonal antibody (as a labelling agent). Detection is carried out using a method of the second aspect of the invention in which the targeting agent and the labelling agent are releasably immobilised to the chromatographic strip.

Experiment Set-Up

Dipstick Design

Figure 2:
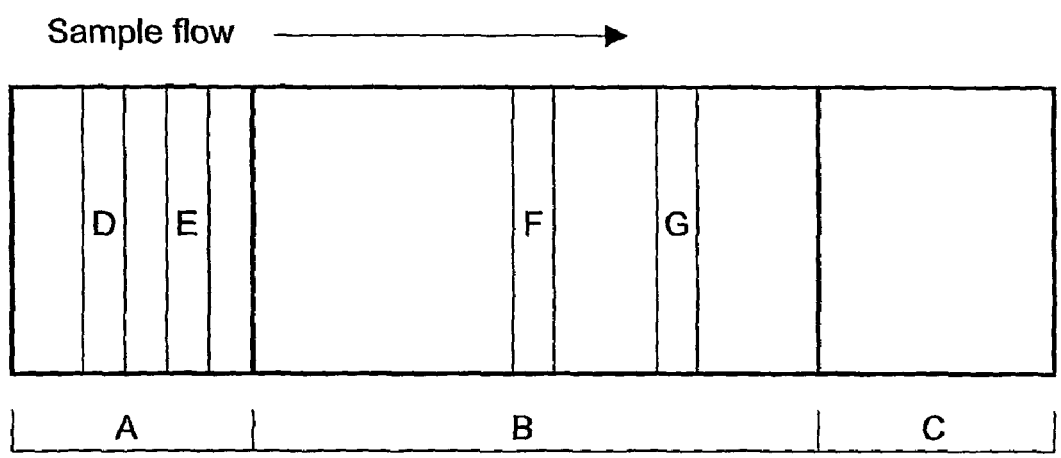
FIG. 2 shows schematically a chromatographic strip used for carrying out embodiments of methods of the invention.

See FIG. 2 which shows a schematic drawing of a chromatographic strip used to perform a method of the invention.

FIG. 2 Shows:

A. Conjugate pad: B. Read-out zone (membrane); C. Absorbent pad; D. Primary antibody=anti-CT-LPS antibody coupled to biotin (targeting agent); E. Secondary antibody=anti-biotin-gold conjugate (labelling agent); F. Specific antibody capture zone; G. Capture zone for control antibody. Membrane may be overlapped between A and B as well as B and C. Sample flow is shown by the bold arrow.

Capture zone, F: a monoclonal antibody (the capture moiety) against a genus-specific CT-LPS epitope is immobilised on the membrane.

Detection reagents (the targeting agent and the labelling agent) for indirect detection of CT according to a method of the invention: an anti-CT-LPS monoclonal antibody coupled to biotin (targeting agent) and an anti-biotin monoclonal antibody coupled to colloidal gold (labelling agent) are deposited onto zones D and E of the conjugate pad.

Detection reagents for direct detection of CT using a conventional method: a colloidal gold labelled anti-CT-LPS monoclonal antibody.

Sample Preparation: Analyte to be Tested:

Men's urine: centrifuge 2 ml of urine, discard the supernatant and resuspend the pellet with sample buffer and heat for 15 min at 100° C.

Sample Buffer:

Standard sample buffer comprising salt, detergent and a blocker (such as BSA or powdered milk).

Sample running: sample extract (100 µl) is added to the conjugate pad (A), or the conjugate pad is immersed in a sample extract. The detection reagents (D&E) are solubilised and begin to move with the sample flow by capillary action along the strip. The molecules of CT-LPS (analyte) present in the sample are bound by the primary antibody (anti-CT-LPS antibody coupled to biotin). Secondary antibody (anti-biotin-gold) conjugates to the biotin on the primary antibody. As the sample passes into the read-out zone (B) and passes over the zone (the capture zone) on which the capture antibody (F) has been immobilised, the complex is trapped. Colour develops in zone F in proportion to the amount of CT-LPS present in the sample.

Procedure control: as a control for direct detection, an anti-mouse-IgG antibody was immobilised at zone G. For indirect detection, an anti-biotin antibody was immobilised at zone G as a control.

Result

See FIG. 3 and Table 1 which shows a comparison of direct and indirect detection as described above. The effect of the molecular ratio of biotin per antibody on assay sensitivity is also shown in Table 1 and in FIG. 7.

TABLE 1

Comparison of direct and indirect detection, and effect of molecular ratio of biotin per antibody on assay sensitivity (using AE99 membrane, a slower flow rate membrane)

| CT-LPS | Direct | Indirect detection (number of biotins per anti-LPS Ab) | | | | | | | |
|---|---|---|---|---|---|---|---|---|---|
| (µl)* | detection | 2 | 4 | 6 | 8 | 9 | 10 | 11 | 12 |
| 0 | 0 | 0 | 0 | 0 | 0 | 0 | 0 | 0 | 0 |
| 0.001 | 0 | 0 | 0 | 0.5 | 2 | 1 | 0.5 | 0.5 | 0.5 |
| 0.003 | 0 | 0 | 0 | 1 | 2 | 2 | 1.5 | 1.5 | 1.5 |
| 0.01 | 0.5 | 0.5 | 0.5 | 2 | 2.5 | 2.5 | 2 | 2 | 2 |
| 0.03 | 1 | 1 | 2.5 | 3 | 4 | 4 | 3.5 | 3.5 | 3.5 |
| 0.1 | 2 | 2.5 | 3 | 4 | 4.5 | 4.5 | 4 | 4 | 4 |

*1 µl contains 4.218 ng of LPS.

The detection signal is on a scale of 1 to 5 with 5 being the strongest.

The results of Table 1 show:

(1) That the amplified detection assay of the invention can detect CT-LPS at a lower concentration than can be detected using the direct detection assay;

(2) The detected signal was amplified (i.e. enhanced) using the assay method of the invention.

Example 2

Assay for HBsAg Detection

Rapid tests are used in some developing countries to screen blood for HBsAg, particularly in blood banks that screen too few samples to justify microtiter plate enzyme immunoassay (EIA) or the considerable expense for the necessary equipment. The most commonly used rapid tests for the detection of HBsAg in developing countries are agglutination, dipsticks and spot tests. Agglutination assays are insensitive, relatively non-specific, subjective and labour intensive. Spot tests require multiple reagents and are unsuitable for medium size throughput and pre-donation screening. In addition, these assays are considerably more expensive than standard EIAs. Dipstick tests are also commercially available, and some of them have high levels of performance. Compared to EIA, the limit of sensitivity of these rapid tests is an order of magnitude lower and results in a lower percentage of HBV infectious blood units detected. EIA itself is 3% less sensitive than genomic amplification (Table 2).

TABLE 2

Detection of HBV infectious blood units by different screening assays

| Assay | Limit of Detection | % of HBV infectious blood units detected* |
|---|---|---|
| Agglutination | 30 ng/ml | 54 |
| Dipstick | 5 ng/ml | 77 |
| EIA | 0.5 ng/ml | 97 |
| Genomic | 40 IU/ml DNA | 100 |

*100% correspond to HBsAg detection by EIA plus HBV DNA detection by PCR in EIA negative blood units Of the available rapid dipstick tests for HBsAg on the market, the Abbott Determine test seems to be the most sensitive (Table 3), with a detection limit of approximately 5 ng/ml, whereas the other tests range from 12-25 ng/ml.

TABLE 3

Comparison of three commercial HBsAg rapid tests

| Company name | HBsAg (ng/ml) | | | |
|---|---|---|---|---|
| | 25 | 12 | 6 | 3 |
| Abbott | 3 | 2 | 1.5 | 0.5 |
| Veda Lab | 2 | 1 | 0 | 0 |
| Alfa Scientific | 1 | 0 | 0 | 0 |

Signals are on a scale of 1 to 5 with 5 being the strongest signal

Aim

To investigate the sensitivity of detection of HBsAg using an anti-HBsAg monoclonal antibody coupled to biotin (targeting agent) and a colloidal gold labelled anti-biotin monoclonal antibody (labelling agent). Detection was carried out using a method of the second aspect of the invention in which the targeting agent and the labelling agent are releasably immobilised to the chromatographic strip.

Experiment Set-Up

Dipstick design : see FIG. 2

For capture line: a polyclonal antibody directed against a genus-specific HBsAg epitope (the 'a' epitope common to all HbsAg subtypes) is immobilised on the membrane (capture moiety).

For Detection:

Direct: a colloidal gold labelled anti-HBsAg monoclonal antibody was used for direct detection using a conventional method.

Indirect: an anti-HBsAg monoclonal antibody coupled to biotin (targeting agent) as well as a colloidal gold labelled anti-biotin monoclonal antibody (labelling agent) are used.

Sample: 50 µl of serum plus 10 µl Tween 20 at 2%.

Running sample: add sample (60 µl) to a container and dip a dipstick into the solution.

Procedure control: an anti-mouse-IgG antibody is immobilised for procedure control.

Result

Figure 4:
FIG. 4 shows results obtained by testing for HBsAg using a conventional method (direct detection) and a method of the invention (indirect detection)
Figure 4:
Figure 4:
Figure 4:
Figure 4:
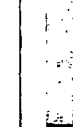
Figure 4:
Figure 4:
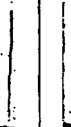
Figure 4:
Figure 4:
Figure 4:
Figure 4:
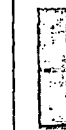
Figure 4:
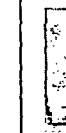
Figure 4:
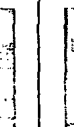
Figure 4:

See FIG. 4 and Table 4.

TABLE 4

Comparison of direct (prior art) and indirect detection (signal enhancement according to the invention) using Purabind A-XP membrane (a faster flow rate membrane)

| HBsAg ng/ml | Direct detection | Indirect detection (number of biotins/anti-HBsAg Ab) | | | | |
|---|---|---|---|---|---|---|
| | | 2 | 4 | 8 | 9 | 10 | 11 |
| 0 | 0 | 0 | 0 | 0 | 0 | 0 | 0 |
| 0.195 | 0 | 0 | 0 | 0.5 | 0.5 | 0 | 0 |
| 0.39 | 0 | 0 | 0 | 1 | 1 | 0.5 | 0.5 |
| 0.78 | 0 | 0 | 0.5 | 1.5 | 1.5 | 1 | 1 |
| 1.56 | 0.5 | 0.5 | 1 | 2.5 | 2.5 | 2 | 2 |
| 3.12 | 1 | 1 | 1.5 | 3.5 | 3.5 | 3 | 3 |
| 6.25 | 1.5 | 2 | 2 | 4.5 | 4.5 | 4 | 4 |
| 12.5 | 2 | 3 | 3 | 5 | 5 | 4.5 | 4.5 |

The detection signal is on a scale of 1 to 5 with 5 being the strongest.

Detection using an indirect detection method of the invention allowed detection of analyte at lower concentrations than by a conventional direct detection method.

For those analyte concentrations at which both methods (direct and indirect) were able to detect analyte (≧1.56 ng/ml), a stronger signal was obtained using indirect detection compared to direct detection.

For the indirect detection method, the optimum number of biotin molecules per molecule of antibody was 8 or 9.

Although one extra antibody is used in indirect detection compared to direct detection, the indirect detection method is still a one-step system.

Figure 11:
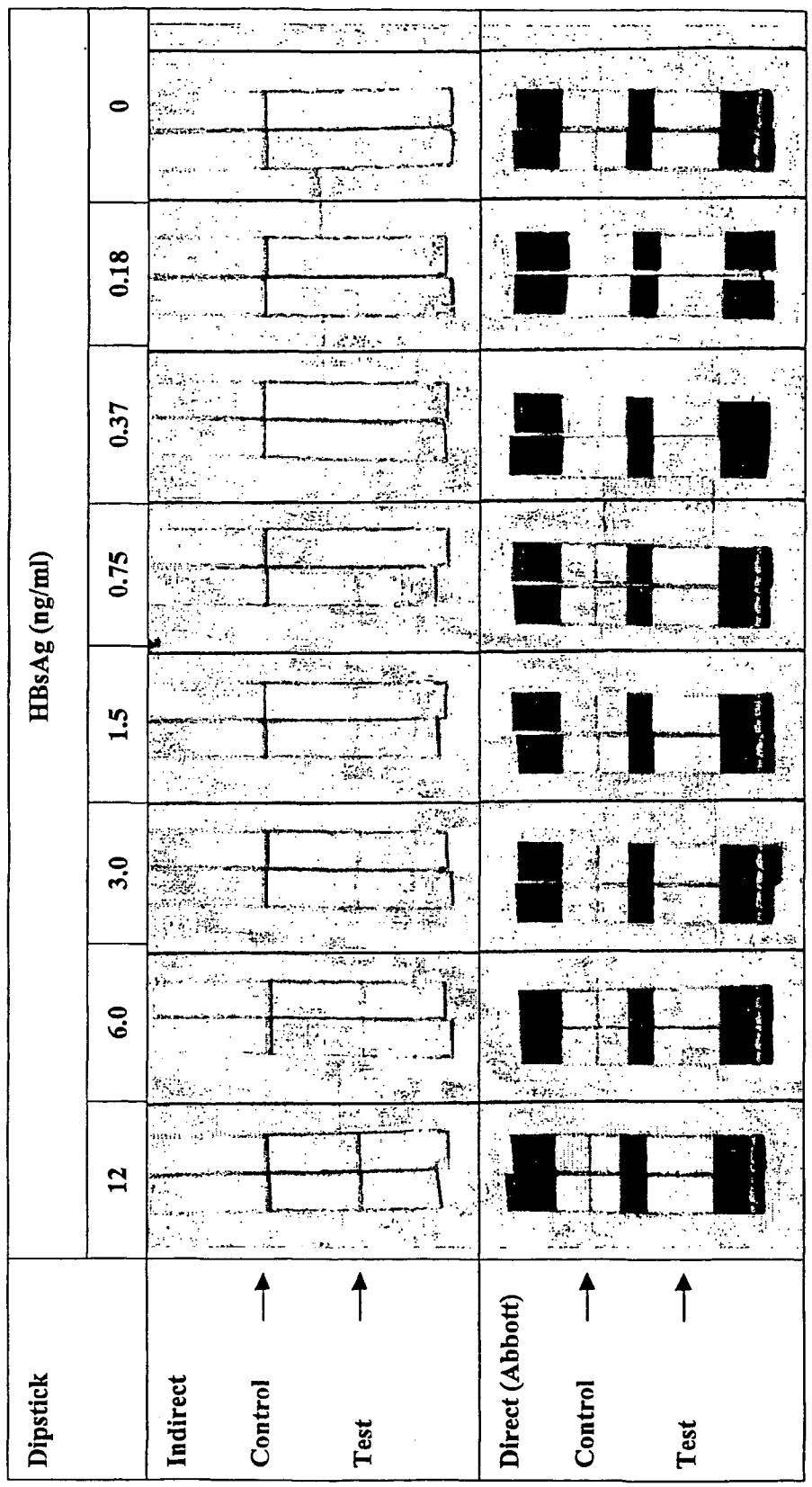
FIG. 11 shows a comparison of HBsAg detection using a method of the invention with a commercially available detection system.

The results of Table 4 also show that indirect detection according to the invention is more sensitive than commercially available rapid tests. To confirm this, the sensitivity of HBsAg detection using a method of the invention was directly compared with the sensitivity of detection using the commercially available Abbott Determine test. The results are shown in Table 5 and FIG. 11.

TABLE 5

Comparison of HBsAg detection between a method of the invention and a commercially available Abbott rapid test

| Dipstick test | HBsAg (ng/ml) | | | | | | |
|---|---|---|---|---|---|---|---|
| | 12 | 6 | 3 | 1.5 | 0.75 | 0.38 | 0.18 | 0 |
| Indirect | 5 | 4 | 3 | 2 | 1.5 | 1 | 0.5 | 0 |
| Direct (Abbott) | 2 | 1.5 | 0.5 | 0 | 0 | 0 | 0 | 0 |

Signals are on a scale of 1 to 5 with 5 being the strongest signal

Discussion and Conclusion from Examples 1 and 2

Compared with the prior art direct detection system, the detection signal was amplified (i.e. enhanced) by using an antibody coupled to biotin and a gold-labelled anti-biotin antibody.

Compared to the sensitivity of HBsAg detection using presently available rapid dipstick tests (approximately 5 ng/ml for the Abbott Determine test, and 12-25 ng/ml for the other tests), tests of the invention are considerably more sensitive, allowing detection of as little as 0.38 ng/ml.

The degree of sensitivity improvement depends on the molecular ratio of biotin per anti-LPS or HBsAg antibody.

The signal was enhanced by increasing the number of molecules of biotin per antibody from 4 to 8 or 9. When an anti-LPS or HBsAg monoclonal antibody was labelled with 8 or 9 biotins, the assay sensitivity increased 30 fold for CT-LPS and 8 fold for HBsAg. The same strength signal (1) is obtained for 0.001 μl CT-LPS using the assay of the invention compared to 0.03 μl CT-LPS using the direct detection prior art assay. The 30-fold increase is particularly surprising because the maximum improvement in the sensitivity of analyte detection is expected to be 8- or 9-fold where 8 or 9 biotins per antibody are used.

Two possible explanations for the increased accumulation of coloured particles using a method of the invention are given below:

(1) The higher the ratio of biotin on antigen specific antibody, the more gold particles captured. However, beyond a certain number of molecules of biotin per antibody, the availability of biotin will not increase. On the contrary, if too many biotins are provided, the reactivity of the antibody with antigen may reduce.

(2) The indirect detection with coloured particles will increase the distance between gold particles and epitope and thus reduce steric hindrance of their binding.

The sensitivity of analyte detection using an indirect method of the invention was reduced when gold-labelled streptavidin was used compared to indirect detection using gold-labelled anti-biotin antibody. This indicates that the sensitivity of detection may be reduced if the distance between the labels and the capture moiety is too little or if the flexibility of the targeting and/or labelling agent is not sufficient.

Two layers of antibody conjugated to coloured particles will further increase the distance between coloured particles and epitope.

The size of the coloured particles used for labelled antis hapten antibody should be optimised to achieve maximum signal. For example, 30 nm colloidal gold is used for CT-LPS assay and for HBsAg assay.

Other ligands could be used, such as FITC (see example 8).

The experiments described in examples 1 and 2 have been repeated using a different indirect method of the invention. Instead of immobilising the biotinylated anti-analyte antibody and anti-biotin gold conjugate to the chromatographic strip, the reagents were mixed with the test solution containing CT-LPS or HBsAg analyte before contacting the mixed solution with the contact end of the chromatographic strip. The results obtained were similar to those obtained for examples 1 and 2. This shows that the improved sensitivity of analyte detection obtained using a method of the invention does not depend on whether the reagents used are immobilised to the chromatographic strip or initially present in the test solution.

Example 3

Optimum Number of Ligands Per Targeting Agent for Membranes of Different Flow Rates We have found that the optimum number of biotins per anti-analyte antibody depends on the flow rate of the dipstick membrane. For slower flow rate membranes (for example Schleicher & Schuell AE99 membrane, pore size 8 μm) optimum results are obtained with about 6-12 ligands per targeting agent, more preferably 8-12 ligands, even more preferably 8-10 ligands, and most preferably 8 or 9 ligands.

Table 6 and FIG. 8 show the effect of the number of biotins per anti-analyte antibody on the sensitivity of analyte detection where a faster flow rate membrane (Whatman Purabind A-RP membrane) is used. Indirect detection according to the invention was carried out by mixing buffer solution containing CT-LPS analyte with biotinylated anti-CT-LPS antibody and anti-biotin gold conjugate and then contacting the mixed solution with the contact end of the chromatographic strip.

TABLE 6

Optimum number of ligands per targeting agent for membranes of different flow rates

| CT-LPS (μl)* | Indirect detection (number of biotins/anti-LPS Ab) | | | | | |
|---|---|---|---|---|---|---|
| | 6 | 9 | 12 | 14 | 18 | 20 |
| 0 | 0 | 0 | 0 | 0 | 0 | 0 |
| 0 | 0 | 0 | 0 | 0.5 | 0.5 | 0 |
| 0.003 | 0 | 0.5 | 0.75 | 1 | 1 | 0.75 |
| 0.01 | 0.5 | 1 | 1.5 | 2 | 2 | 1.5 |
| 0.03 | 1 | 2 | 2.5 | 3.5 | 3.5 | 2.5 |
| 0.1 | 2 | 3 | 3.5 | 4.5 | 4.5 | 4 |

*1 μl contains 4.218 ng of LPS
Signals are on a scale of 1 to 5 with 5 being the strongest signal.

To obtain a signal strength of 1 using an indirect detection method of the invention when only 0.0031 μl of CT-LPS are present, the biotinylated antibody should contain 14-18 biotins. Thus, the number of biotins per biotinylated anti-CT-LPS antibody should be optimized for the flow rate of the membrane used.

Example 4

Comparison of One-Step and Two-Step Methods

In this example, the sensitivity of detection of CT-LPS analyte using a one-step assay (in accordance with an embodiment of the first aspect of the invention) and a two-step assay (not according to the invention) were compared.

To perform the one-step and two-step assays, a dipstick (Purabind A-RP membrane, a fast flow rate membrane) comprising a contact end and an antibody (the capture antibody) immobilised to a capture zone of the dipstick remote from the contact end was used. The capture antibody is capable of binding to the CT-LPS analyte (an anti-CT-LPS antibody). A biotinylated anti-CT-LPS antibody comprising 14 biotins per antibody (the targeting agent) and anti-biotin antibody labelled with colloidal gold (the labelling agent) were used to detect the CT-LPS analyte.

The one-step assay was carried out by mixing a test solution containing CT-LPS with biotinylated anti-CT-LPS antibody and anti-biotin-antibody-gold conjugate, then contacting the mixed solution with the contact end of the dipstick, allowing the solution to reach the capture zone by capillary action, and detecting for the presence of gold label at the capture zone. Thus, the analyte, targeting agent and labelling agent are wicked up the dipstick simultaneously in a single step.

The two-step assay was carried out by mixing 50 μl buffer solution with CT-LPS and biotinylated anti-CT-LPS antibody, then contacting the mixed solution with the contact end of the dipstick, and allowing the solution to reach the capture zone by capillary action. Then, the contact end of the dipstick was contacted with 100 μl of a suspension of the anti-biotin-gold conjugate, and this was allowed to travel to the capture zone by capillary action. Then, the presence of gold label was detected for at the capture zone. Thus, the targeting agent and labelling agent are wicked up the dipstick separately in two distinct steps.

The results of the comparison of the one-step and two-step assays are shown in table 7 and FIG. 9.

TABLE 7

Comparison of one-step and two-step assays

| CT-LPS (μl)* | One-step | Two-step |
|---|---|---|
| 0 | 0 | 0 |
| 0.001 | 0.5 | 0 |
| 0.003 | 1 | 0 |
| 0.01 | 2 | 0.5 |
| 0.03 | 3 | 1 |
| 0.1 | 4.5 | 2 |

*1 μl contains 4.218 ng of LPS
Signals are on a scale of 1 to 5 with 5 being the strongest signal.

The results of Table 7 and FIG. 9 show that the sensitivity of CT-LPS detection using the one-step CT-LPS assay is 10 times greater than the two-step CT-LPS assay (the same strength signal (1) is obtained for 0.003 μl of CT-LPS using the one-step assay as with 0.03 μl CT-LPS using the two-step assay).

We have also found that the quality and visibility of the signal line produced at the capture zone of the dipstick is greater for the one-step assay than the two-step assay.

Example 8

Use of FITC as Targeting Agent Ligand

In this example the sensitivity of analyte detection using direct and indirect detection methods was again compared. However, here the ligand used in the indirect detection method was fluorescein isothiocyanate (FITC) rather than biotin. Direct (prior art) detection was carried out using a similar method to that described in Example 1. Indirect detection according to the invention was carried out by mixing buffer solution containing CT-LPS analyte with FITC coupled to anti-CT-LPS antibody and anti-FITC antibody labelled with colloidal gold. Then the mixed solution was contacted with the contact end of the chromatographic strip. The number of FITC ligands per anti-analyte antibody was varied. The results obtained are shown in Table 8 and FIG. 10, and are very similar to those obtained for Example 1. The optimum number of FITC molecules per anti-CT-LPS antibody is about 7-11.

TABLE 8

Use of FITC as a targeting agent ligand (AE99 membrane)

| CT-LPS | Direct | Indirect detection (number of FITCs/anti-LPS Ab) | | | |
|---|---|---|---|---|---|
| (μl) * | detection | 6 | 7 | 9 | 11 |
| 0 | 0 | 0 | 0 | 0 | 0 |
| 0.001 | 0 | 0 | 1 | 1 | 1 |
| 0.003 | 0 | 0.5 | 2 | 2 | 2 |
| 0.01 | 0.5 | 1 | 2.5 | 2.5 | 2.5 |
| 0.03 | 1 | 2 | 3.5 | 4 | 3 |
| 0.1 | 2 | 3 | 4.5 | 4.5 | 4 |

* 1 μl contains 4.218 ng of LPS
Signals are on a scale of 1 to 5 with 5 being the strongest signal.

These results demonstrate that the improved sensitivity of analyte detection obtained using an indirect method of the invention is not restricted to the use of biotin.

FIGURE LEGENDS

Figure 1:
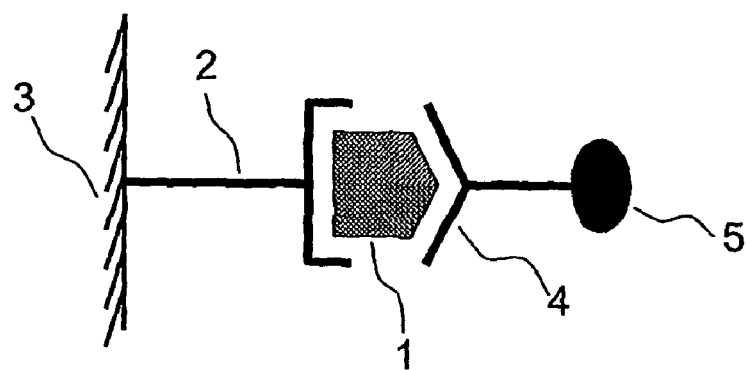
FIG. 1 shows schematically a comparison of conventional analyte detection with analyte detection according to an embodiment of the invention.
Figure 1:
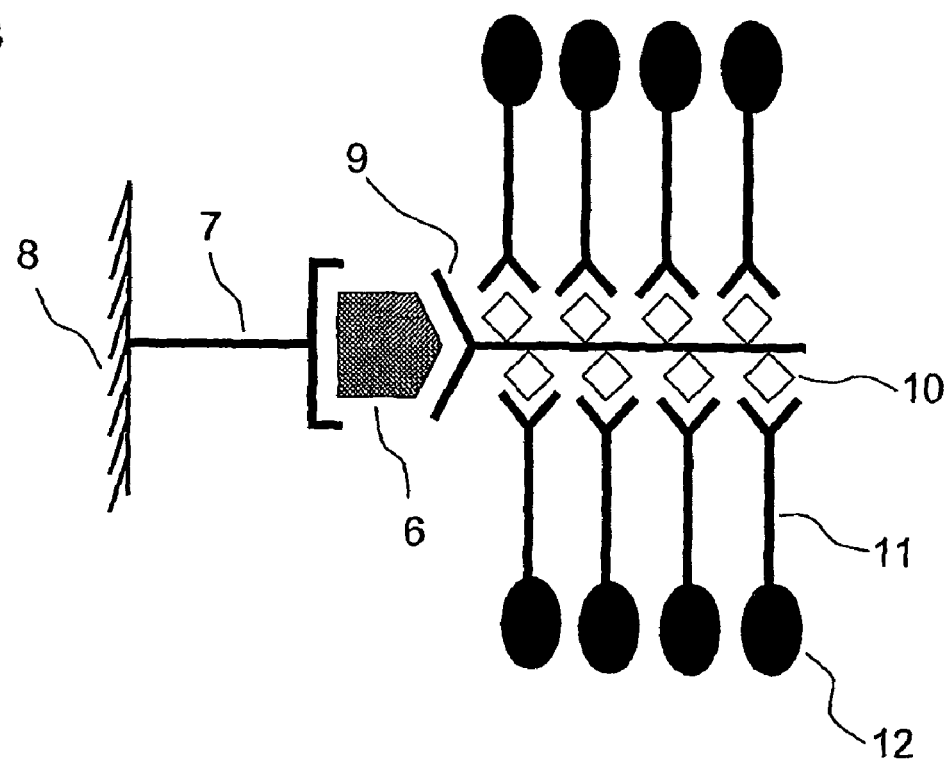

FIG. 1
A) Schematic representation of conventional detection of analyte (direct detection). The figure shows a CT bacterium (1) bound by an anti-LPS antibody (2) immobilised to a solid phase (3) and an anti-LPS antibody (4) labelled with colloidal gold (5) bound to the CT bacterium (1).
B) Schematic representation of detection of analyte according to an embodiment of the invention. The FIG. shows a CT bacterium (6) bound by an anti-LPS antibody (7) immobilised to a solid phase (8) and an anti-LPS antibody (9) coupled to 8 biotins (10) [(9) and (10) form the targeting agent]. Each biotin is bound by an anti-biotin antibody (11) labelled with colloidal gold (12) [(11) and is (12) form the labelling agents].

Figure 5:
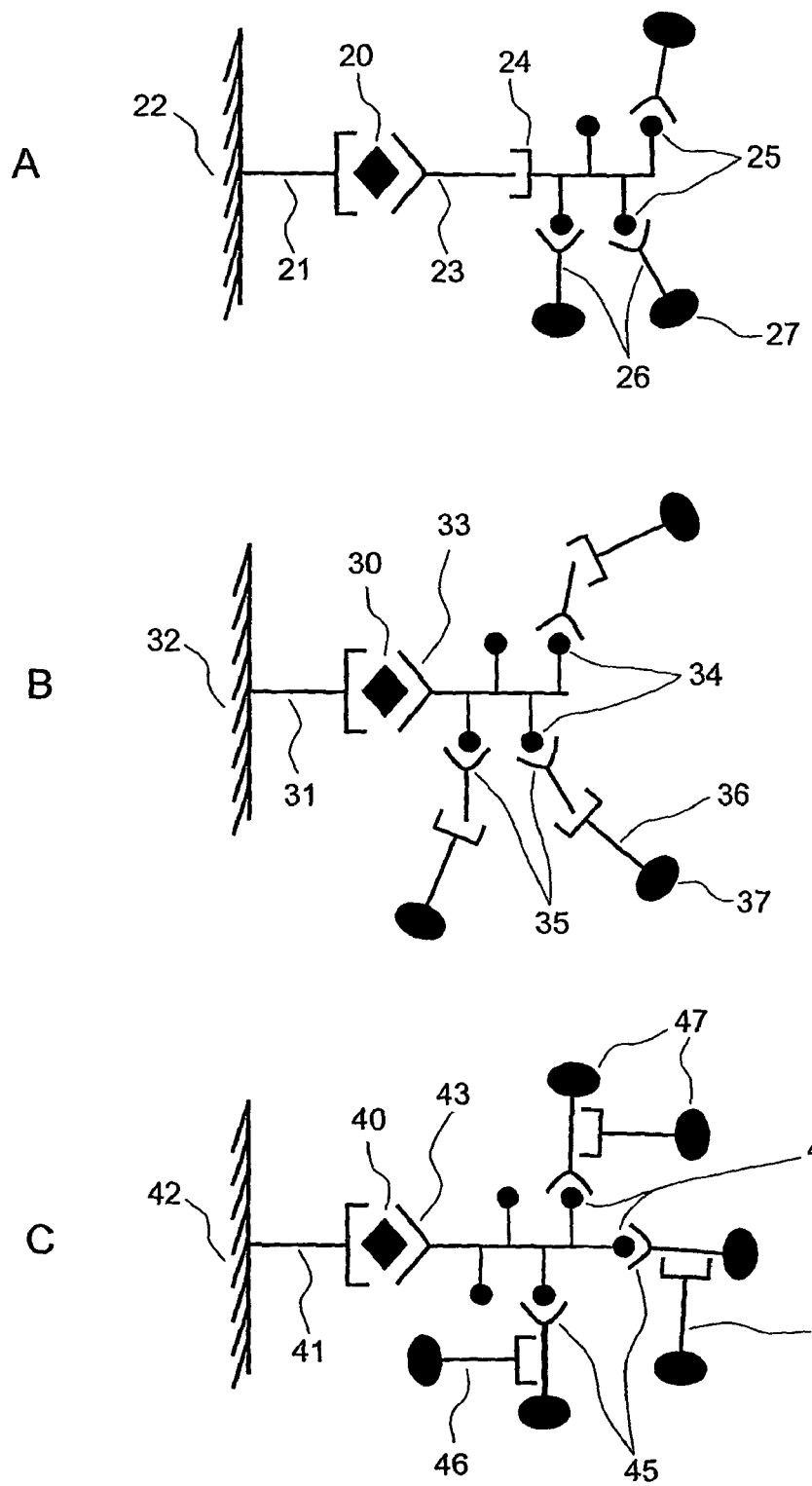
FIG. 5 shows examples of embodiments of the invention.

FIG. 5
Different embodiments of the invention are shown schematically:
A) Analyte (20) captured by a capture moiety (21) immobilised to a solid phase (22). A primary moiety (23) [for example an anti-analyte mouse antibody] of the targeting agent is bound to the analyte (20) and is itself bound by a secondary moiety (24) [for example an anti-mouse antibody] of the targeting agent. The secondary moiety (24) comprises a plurality of ligands (25). The ligands are bound by labelling agents (26) comprising labels (27) [for example anti-ligand antibodies conjugated with coloured particles].
B) Analyte (30) captured by a capture moiety (31) immobilised to a solid phase (32). A targeting agent (33) [for example an anti-analyte antibody] provided with a plurality of ligands (34) is bound to the analyte (30) and is itself bound by a plurality of primary moieties (35) [for example anti-ligand mouse antibodies] of the labelling agent. Each primary moiety (35) is bound by a secondary moiety (36) of the labelling agent comprising a label (37) [for example an anti-mouse antibody conjugated with a coloured particle].
C) Analyte (40) captured by a capture moiety (41) immobilised to a solid phase (42). A targeting agent (43) provided with a plurality of ligands (44) is bound to the analyte (40) and is itself bound by a plurality of labelled primary moieties (45) of the labelling agent. Each labelled primary moiety (45) is bound by a labelled secondary moiety (46) of the labelling agent. The labels are shown as (47).

Figure 6:
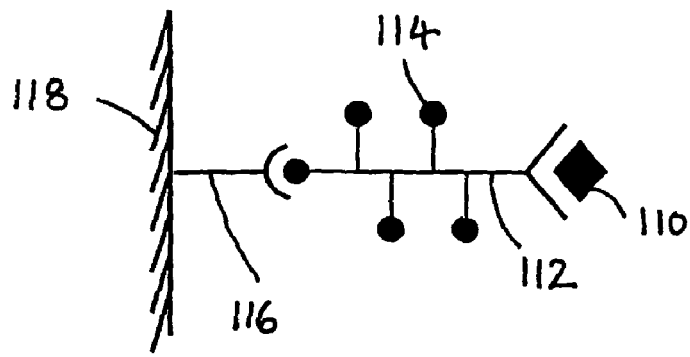
FIG. 6 shows examples of derivatising moieties captured with the analyte by a capture moiety (note that binding of analyte by labelled targeting agent is not shown)
Figure 6:
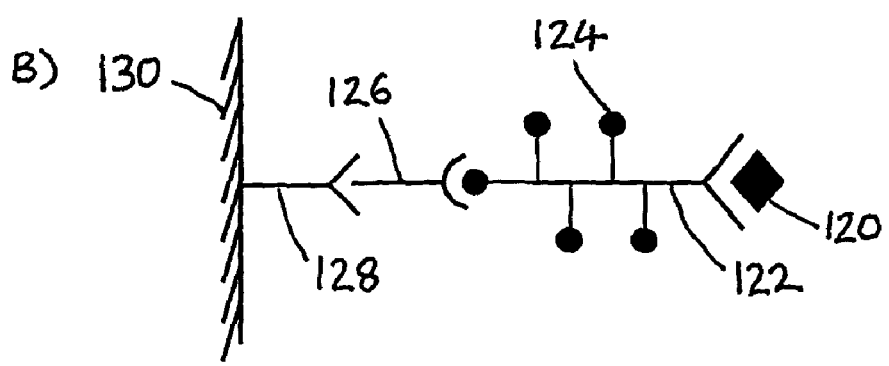
Figure 6:
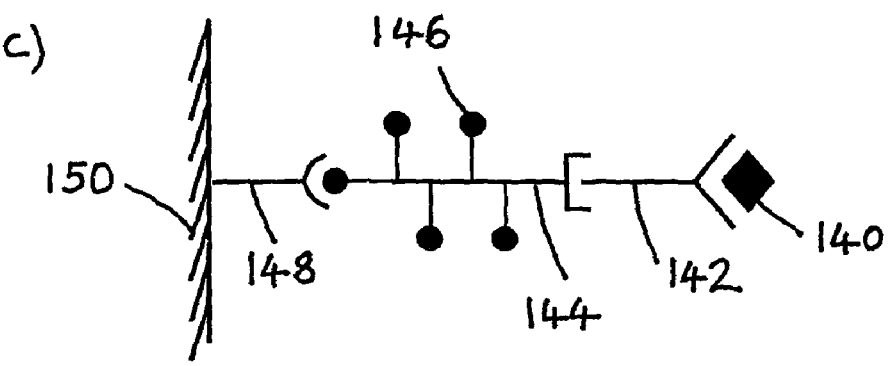

FIG. 6
Further embodiments of the invention are shown schematically:
A) Analyte (110) bound to a derivatising moiety (112) provided with a plurality of ligands (114) captured by a capture moiety (116) immobilised to a capture zone of the chromatographic strip (118).
B) Analyte (120) bound to a first derivatising moiety (122) provided with a plurality of ligands (124). A second derivatising moiety (126) is bound to a ligand of the first derivatising moiety. The second derivatising moiety is captured by a capture moiety (128) immobilised to a capture zone of the chromatographic strip (130).
C) Analyte (140) bound to a first derivatising moiety (142). A second derivatising moiety (144) bound to the first derivatising moiety is provided with a plurality of capture ligands (146). A capture moiety (148) immobilised to a capture zone of chromatographic strip (150) binds to one of the capture ligands.

This application claims priority to GB0029154.2, filed Nov. 30, 2000, and GB0109313.7, filed Apr. 17, 2001, the entirety of which is hereby incorporated by reference.

The invention claimed is:

1. A method for testing for the presence of an analyte in a test solution comprising:
  a) providing a chromatographic strip having a contact end for contacting the test solution and a capture moiety immobilized at a capture zone of the chromatographic strip, the capture moiety comprising a member of a ligand/anti-ligand binding pair capable of binding the analyte, or a derivative thereof, as the other member of the ligand/anti-ligand binding pair, wherein the binding is not by a nucleic acid base pairing interaction;
  b) contacting the contact end of the chromatographic strip with the test solution to allow analyte, or derivative thereof, to travel to the capture zone by capillary action and be captured by the capture moiety;
  c) contacting a labeled targeting agent with the capture zone, the labeled targeting agent being capable of binding the analyte, or a derivative thereof, thereby allowing labeled targeting agent to be captured at the capture zone as part of a complex comprising the capture moiety, the analyte or derivative and the labeled targeting agent, wherein the labeled targeting agent comprises a plurality of ligands and each of two or more ligands are bound to a label, and wherein the labels are bound to the ligands before the labeled targeting agent is contacted with the capture zone; and
  d) detecting for the presence of label at the capture zone.

2. A method for testing for the presence of an analyte in a test solution comprising:
  a) providing a chromatographic strip having a contact end for contacting the test solution and a capture moiety immobilized at a capture zone of the chromatographic strip, the capture moiety comprising a member of a ligand/anti-ligand binding pair capable of binding the analyte, or a derivative thereof, as the other member of the ligand/anti-ligand binding pair, wherein the binding is not by a nucleic acid base pairing interaction;
  b) contacting the contact end of the chromatographic strip with the test solution to allow analyte, or derivative thereof, to travel to the capture zone by capillary action and be captured by the capture moiety;
  c) contacting a targeting agent, capable of binding the analyte, or derivative thereof, with the capture zone to allow targeting agent to bind to analyte or derivative captured at the capture zone, the targeting agent being provided with a plurality of ligands, each of two or more ligands of the targeting agent being bound to a label, wherein the labels are bound to the ligands before the targeting agent is contacted with the capture zone; and
  d) detecting for the presence of label at the capture zone.

3. The method according to claim 1, wherein the labeled targeting agent is formed by binding of the labels to ligands of a targeting agent, wherein the targeting agent is capable of binding the analyte, or a derivative thereof, and the targeting agent comprises a plurality of ligands, wherein binding of the labels to the ligands of the targeting agent to form the labeled targeting agent is carried out in the test solution.

4. The method according to claim 3, wherein the labels are provided by labeling agents which are added separately to the test solution at substantially the same time as the labeled targeting agent is contacted with the test solution.

5. The method according to claim 3, wherein the targeting agent is pre-incubated with the test solution before the labels are bound to the ligands of the targeting agent.

6. The method according claim 1, wherein a plurality of labels are bound to at least one of the ligands of the labeled targeting agent.

7. The method according to claim 1, wherein the analyte is a CT analyte, or an HBsAg.

8. A method according to claim 1, wherein the chromatographic strip and the labeled targeting agent are provided by a kit which comprises:
  (i) a chromatographic strip having a contact end for contacting the test solution and a capture moiety immobilised at a capture zone of the chromatographic strip, the capture moiety comprising a member of a ligand/anti-ligand binding pair capable of binding the analyte, or a derivative thereof, as the other member of the ligand/ anti-ligand binding pair, wherein the binding is not by a nucleic acid base pairing interaction; and
  (ii) separately from the chromatographic strip: a targeting agent capable of binding the analyte, or a derivative thereof, wherein the targeting agent comprises a plurality of ligands; and a plurality of labels;
  wherein the labels are bound to the ligands of the targeting agent to form the labeled targeting agent before the labeled targeting agent is contacted with the capture zone.

* * * * *